United States Patent [19]

Paul

[11] Patent Number: 5,707,356
[45] Date of Patent: Jan. 13, 1998

[54] PRESSURE RELIEF VALVE

[75] Inventor: Gregory L. Paul, Salem, N.H.

[73] Assignee: Medtronic, Inc., Minneapolis, Minn.

[21] Appl. No.: 640,424

[22] Filed: Apr. 30, 1996

[51] Int. Cl.⁶ ................................................ A61M 1/00
[52] U.S. Cl. ................... 604/119; 604/118; 604/247; 604/167
[58] Field of Search ...................... 604/167, 169, 604/118, 119, 247

[56] References Cited

U.S. PATENT DOCUMENTS

| | | | |
|---|---|---|---|
| 3,556,122 | 1/1971 | Laerdal | 137/102 |
| 3,572,375 | 3/1971 | Rosenberg | 137/512 |
| 3,626,978 | 12/1971 | Hoekstra | 137/525.3 |
| 3,633,613 | 1/1972 | Julow | 137/512.3 |
| 3,661,174 | 5/1972 | Cripe | 137/512.3 |
| 3,818,929 | 6/1974 | Braukmann | 137/218 |
| 3,905,382 | 9/1975 | Waterston | 137/102 |
| 3,941,149 | 3/1976 | Mittleman | 137/493.1 |
| 4,084,606 | 4/1978 | Mittleman | 137/102 |
| 4,502,502 | 3/1985 | Krug | 604/118 |
| 4,642,097 | 2/1987 | Siposs | 604/118 |
| 4,671,786 | 6/1987 | Krug | 604/4 |
| 4,758,224 | 7/1988 | Siposs | 604/119 |
| 5,290,263 | 3/1994 | Wigness | 604/247 |
| 5,401,255 | 3/1995 | Sutherland | 604/247 |

*Primary Examiner*—Sam Rimell
*Assistant Examiner*—Luke J. Yeh
*Attorney, Agent, or Firm*—Harold R. Patton; Curtis D. Kinghorn; Peter Forrest

[57] ABSTRACT

An overpressure safety valve assembly for use during heart surgery is disclosed. The assembly comprises an elongated tubular body portion having an inlet end, and an outlet end and an unidirectional valve disposed therebetween. A relief valve portion is joined to and in flow communication with the tubular portion. The relief valve portion includes a first relief valve configured to open if the pressure within the overpressure safety valve diminishes below a predetermined level, and a second relief valve configured to open if the pressure adjacent the outlet end exceeds a predetermined level. The first and second relief valves are disposed in a side by side configuration in a common conduit.

9 Claims, 3 Drawing Sheets

PRESSURE RELIEF VALVE

BACKGROUND OF THE INVENTION

1. Field of the Invention

This invention relates to the field of vent valves, and more particularly to a vent valve assembly used in heart surgery.

2. Prior Art

During heart surgery, a drainage cannula is often inserted into the heart and more specifically, into the left ventricle. This cannula is used to drain the blood either by gravity flow or in combination with a pump. The blood is directed through one or more conduits to a cardiotomy reservoir, and then to an oxygenator which oxygenates the blood. Blood flow is then directed back to the patient. It has been found in connection with such a system, that certain advantages can be gained by decompressing the left ventricle during the cardiopulmonary bypass procedure. One of the problems associated with pump drainage is excessive suction. While the mount of suction can be increased, too much suction can cause the conduits to collapse should the drainage cannula become occluded. Even though this problem has been recognized for some time, the solution has proved elusive.

The prior art is well aware of many valve configurations which have been used in a wide variety of medical products as well as in connection with automotive products, and the like. Examples of such valves are disclosed in U.S. Pat. Nos. 3,556,122; 3,572,375; 3,626,978; 3,633,613; 3,661,174; 3,818,929; 3,905,382; 3,941,149; and 4,084,606. Notwithstanding the existence of these different valve configurations, there is no prior art device which has all of the features associated with the overpressure safety valve of the present invention.

In particular, an overpressure safety and one way valve assembly is described in U.S. Pat. No. 4,502,502 entitled "Overpressure Safety Valve" and issued to John A. Krug on Mar. 5, 1985 and assigned to C. R. Bard, Inc. of Murray Hill, N.J. In this valve assembly, an elongated tubular body portion contains a one-way valve. An inlet end of the tubular body portion connects to a conduit that in turn is connected to a drainage cannula. An opposite outlet end of the tubular body portion is connected to a conduit that is in turn connected to a pump for moving blood through an extracorporeal bypass system. The one-way valve allows blood to flow through the tubular body portion only in a direction from the drainage cannula to the pump.

The Krug invention also has a pair of pressure relief valves. These first of these valves act as a negative pressure relief valve to limit vacuum pressure in the line to a desired pressure, typically approximately 190 mm Hg. In use, should the pressure within the overpressure safety valve decrease to this desired pressure, this first overpressure relief valve would open thus permitting air to be drawn into the tubular body portion. In this manner, a potentially dangerous sucking action on the cannula side of the valve assembly is substantially diminished.

The second pressure relief valve operates as a positive pressure relief valve to relieve any pressure buildup in the line between the pump and the valve assembly. In use, should the pressure increase adjacent the outlet end, for example due to the pump action being inadvertently reversed, the increased pressure causes the second valve to open and thus release the pressure buildup.

In the Krug invention, both pressure relief valves are "umbrella" type valves that are located adjacent to the tubular body portion in a linear configuration, that is, with one valve located in-line with the other valve along an axis parallel to the elongated axis of the tubular body portion. It is often desirable to visually monitor the status of these relief valves. The Krug design does not allow both valves to be viewed at once.

SUMMARY OF THE INVENTION

The overpressure safety valve assembly of the present invention comprises an elongated tubular body portion having an inlet end and an outlet end. The inlet end of the valve is connected to a conduit which, in turn, is connected to a cannula inserted into the left ventricle of the heart. The outlet end of the valve is connected to a conduit which, in turn, is connected to a cardiotomy reservoir. A pump, such as is well known in the art, draws blood from the left ventricle, through the various conduits and the subject cannula vent valve, and into the cardiotomy reservoir. In order to insure blood flow in one direction, a unidirectional flow regulator is disposed along the length of the tubular body portion.

A relief valve portion is joined to and in flow communication with the tubular body portion. The relief valve portion includes a first relief valve configured to open if the pressure adjacent the outlet end diminishes below a predetermined level, and a second relief valve configured to open if the pressure adjacent the outlet end exceeds a predetermined level. In this manner, unrestricted blood flow from the left ventricle of the heart to the cardiotomy reservoir can be achieved, but backflow into the heart through the conduit is precluded. In addition, the first relief valve limits the vacuum in the line to a predetermined level thereby preventing damage to tissues, especially heart tissues, if the line between the heart and the vent valve assembly becomes occluded. The second relief valve acts as a positive pressure relief valve and relieves any pressure buildup in the line between the pump and the vent valve assembly. The first and second relief valves are arranged in a side by side configuration so that both valves can be visually inspected at the same time to ascertain their status.

The novel features which are believed to be characteristic of the invention, both as to its organization and method of operation, together with further advantages and objectives thereof, will be better understood from the following description considered in connection with the accompanying drawings in which a presently preferred embodiment of the invention is illustrated by way of example. It is to be expressly understood, however, that the drawings are for the purpose of illustration and description only, and are not intended as a definition of the limits of the invention.

DETAILED DESCRIPTION OF THE INVENTION

Figure 1:
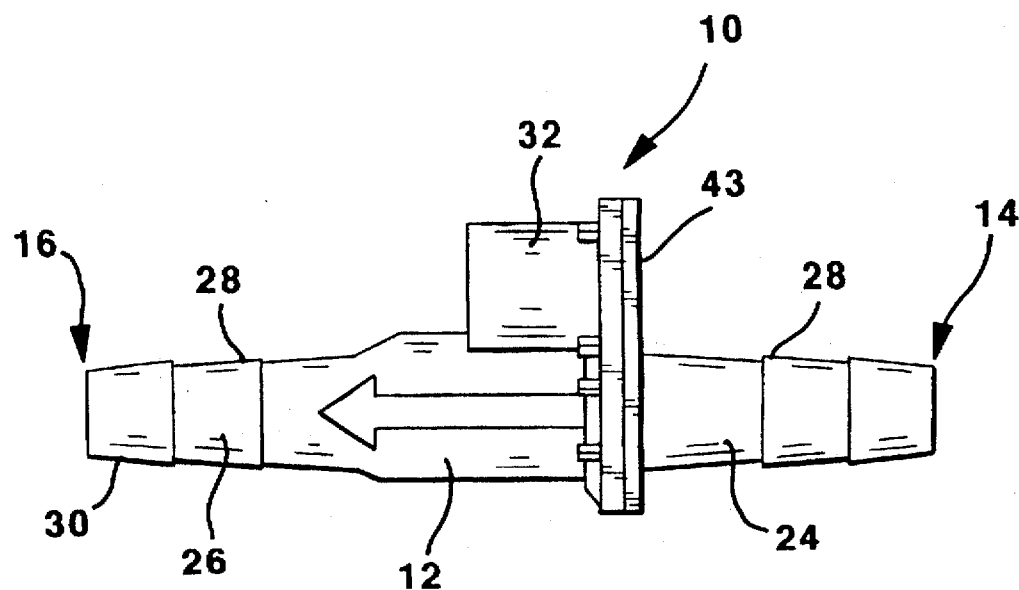
FIG. 1 is a side elevational view of the overpressure safety valve assembly of the present invention.
Figure 2:
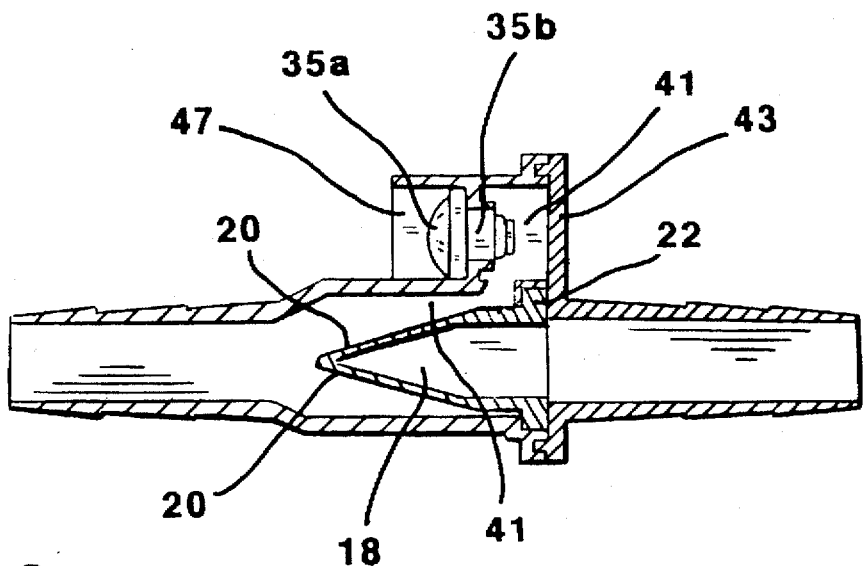
FIG. 2 is a cutaway view of the overpressure safety valve assembly of the present invention shown in FIG. 1.

Referring first to FIGS. 1 and 2, there is shown, as a presently preferred embodiment, an overpressure safety valve assembly 10 which is comprised of an elongated tubular body portion 12 having an inlet end 14 and an outlet end 16. A unidirectional flow regulator or valve 18 is axially disposed in the body 12 along the length thereof. Such unidirectional valve 18 is well known and recognized in the art sometimes being referred to as a "duckbill" valve. Such a valve 18 includes flap members 20 and an integral base 22 defining a generally cylindrical base opening. Valve body portion 12 is made of a first tubular section 24 and a second tubular section 26 joined together so as to sandwich the base 22 of the valve 18 therein between. Each end 14, 16 of the body 12 has a series of ribbed or barbed members 28 which enable the assembly 10 to be easily joined to flexible conduits as herein below described in greater detail. While each of the sections 24, 26 have preselected diameters, in the preferred embodiment, a reduced diameter portion 30 forms outlet end 16.

Joined to and in flow communication with the tubular body portion 12 is a tubular relief valve portion 32. Relief valve portion 32 includes two inline poppet relief valves 34, 36. Such relief valves 34, 36 are also well known in the art, and sometimes referred to as "umbrella" valves, and include an outwardly extending head 35a and an elongated body 35b. Valves 34, 36 are held in side by side alignment in relief valve portion 32 across tubular body portion 12. Relief valve portion 32 has a central chamber 41 that is connected to the tubular body portion 12 through a trough-like flow channel 40. Channel 40 allows pressure to be communicated from tubular body portion 12 to central chamber 41.

Chamber 41 is defined on one side by a wall 43 and on the opposite side by an ambient air conduit 47 that is open to ambient air pressure. A pair of mounting flanges 38a and 38b are located in ambient air conduit 47 and form associated valve seats for each of the valves 34, 36, respectively. Ambient air conduit 47 contains both valves 34 and 36. Mounting flanges 38a,b in ambient air conduit 47 position valves 34,36 in opposite directions so that extending head 35a for valve 34 extends toward chamber 41 while extending head 35a for valve 35 extends away from chamber 41 toward the ambient air. In this way, both extending head 35a for valve 34 and elongated body 35b for valve 36 are directed toward chamber 41. Similarly, extending head 35a for valve 36 and elongated body 35b for valve 34 are directed toward the ambient air side of ambient air conduit 47. By placing both valve 34, 36 in the same conduit, that is ambient air conduit 47, the status of both valves 34, 36 can be visually ascertained at the same time. In other words, with a single glance, it can be visually ascertained the conditions of valves 34, 36.

Figure 3:
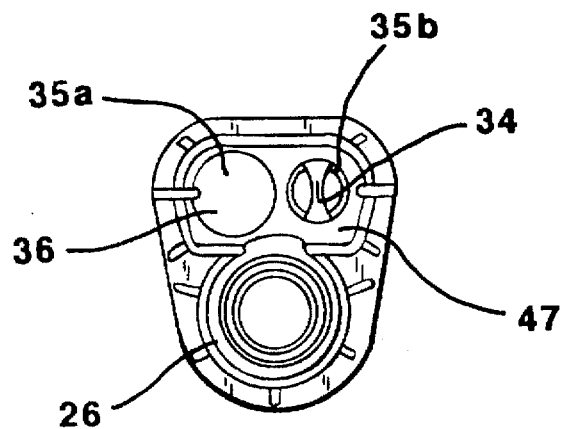
FIG. 3 is an end view of one end of the overpressure safety valve assembly of the present invention shown in FIG. 1.
Figure 4:
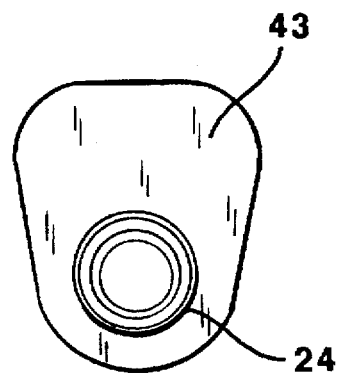
FIG. 4 is an end view of the opposite end of the overpressure safety valve assembly of the present invention shown in FIG. 3.
Figure 5:
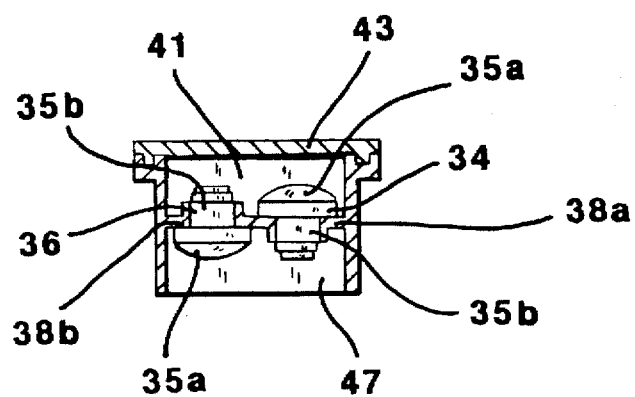
FIG. 5 is a top sectional view of the overpressure safety valve assembly of the present invention shown in FIG. 1.
Figure 6:
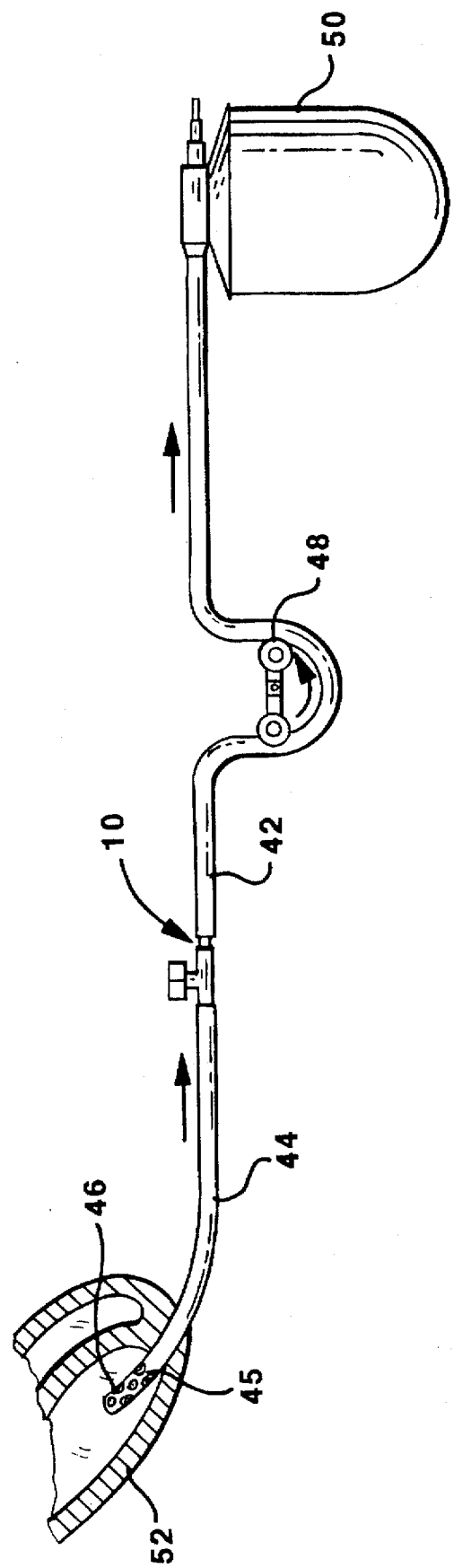
FIG. 6 is a circuit diagram showing the use of the overpressure safety valve assembly of the present invention.

Referring now to FIG. 3, a circuit diagram is illustrated which shows how the overpressure safety valve assembly 10 of the present invention is utilized. Preferably, a first conduit 42 is joined to the outlet end 16 of the assembly 10, while a second conduit 44 is joined to the inlet end 14. Conduit 44, in turn, is connected to a cannula 45 which, typically, has a series of openings 46 adjacent its distal end. Openings 46 permit the left ventricle of the heart 52 to be drained such as is typically done during a cardiopulmonary bypass operation. In order to insure quick drainage of the left ventricle of the heart 52, a pump 48 is disposed on the outlet side of the valve assembly 10. Such a pump 48 is the Model BP-80 centrifugal blood pump sold by Medtronic-BioMedicus of Eden Prarie, Minn.

In an alternate embodiment, pump 48 includes a roller member which rolls along conduit 42 thereby creating a vacuum in conduit 44 and cannula 45. Thus, the blood from the left ventricle of the heart 52 is drawn into the cannula 45 and conduit 44, and through the vent valve assembly 10. Once past the pump 48, the blood is pushed through the remainder of conduit 42 into cardiotomy reservoir 50.

In the operation of the subject overpressure safety valve assembly 10, blood would flow into the inlet end 14 of the valve body portion 12. Sufficient pressure would cause the flap members 20 to open enabling blood to flow through the valve body portion 12 and out the outlet end 16. If for some reason the pump was inadvertently operated such that a "backflow" was created, back pressure would cause the flap members 20 to close thereby preventing flow back into the heart 52. In this manner, the unidirectional valve 18 allows blood flow from the left ventricle of the heart 44 to the cardiotomy reservoir 50, but closes automatically to prevent flow back into the heart.

The first umbrella relief valve 34 operates as a negative pressure relief valve in that it limits the vacuum in the line to approximately 190 mm Hg. That is, should the pressure within the overpressure safety valve decrease to this pressure, umbrella valve 34 would open thus permitting air to be drawn into the body portion 12. In this manner, a potentially dangerous sucking action on the up stream side of the assembly 10 (i.e., in the cannula 45 and heart 44) would be substantially diminished.

The second umbrella relief valve 36 operates as a positive pressure relief valve in that it relieves any pressure buildup in conduit 42 between the pump 48 and the valve assembly 10. More specifically, should the pressure increase adjacent the outlet end 16 (for example should the pump action be inadvertently reversed) such increase pressure will cause umbrella valve 36 to open thus releasing the pressure buildup.

While the preferred embodiment of the present invention has been described by reference to FIGS. 1–3, it will be apparent to those skilled in the art that various other applications of the valves are possible. For example, other types of unidirectional flow regulators are within the scope of the present invention. In the preferred embodiment, the flow axis of members 12 and 32 are substantially parallel; other flow axes are also within the scope of this invention. Further, the preferred embodiment of the present invention contemplates the use of polycarbonate plastics for the elements 12 and 32. Other similar biocompatible materials are also within the scope of the present invention. This invention, therefore, is not intended to be limited to the particular embodiments herein disclosed.

What is claimed is:

1. An overpressure safety valve assembly comprising:
  a) an elongated tubular body portion having
    i) an inlet portion having a first end including means adapted to be connected to a conduit and an opposite second end, and an outlet portion having a first end including means adapted to be connected to a conduit and an opposite second end, the second ends of the tubular body portion being complimentally configured to each other such that when joined together, form a flow path through the tubular body, and
    ii) a unidirectional flow regulator valve having mounting means adapted to be sandwiched between the second ends of the inlet and outlet portions, the second ends of the inlet and outlet portions of the tubular body portions including means configured to receive the mounting means therebetween, the unidirectional flow valve permitting flow through the tubular body portion only from the inlet portion to the outlet portion;

b) a relief valve portion joined to the tubular body portion, the relief valve portion having a central chamber, the central chamber having a single common ambient air conduit open to ambient air pressure;

c) a flow channel extending between the central chamber and the tubular body portion, the flow channel providing fluid communication between the tubular body portion and the central chamber;

d) a first relief valve mounted in the ambient air conduit and configured to open if the pressure within the overpressure safety valve assembly diminishes below a predetermined level; and e) a second relief valve mounted in the ambient air conduit and configured to open if the pressure within the overpressure safety valve assembly exceeds a predetermined level.

2. An overpressure safety valve assembly according to claim 1 in which the unidirectional flow regulator valve has a duckbill configuration.

3. An overpressure safety valve assembly according to claim 1 in which the first and second relief valves are disposed in a side by side configuration.

4. An overpressure safety valve assembly according to claim 1 in which the first and second relief valves are each umbrella-type valves.

5. An overpressure safety valve assembly comprising:

an elongated tubular body portion having i) an inlet portion having a first end including means adapted to be connected to a conduit and an opposite second end, and an outlet portion having a first end including means adapted to be connected to a conduit and an opposite second end, the second ends of the tubular body portion being complimentally configured to each other such that when joined together, form a flow path through the tubular body, and ii) a unidirectional flow regulator valve having mounting means adapted to be sandwiched between the second ends of the inlet and outlet portions, the unidirectional flow regulator valve has a duckbill configuration, the second ends of the inlet and outlet portions of the tubular body portions including means configured to receive the mounting means therebetween, the unidirectional flow valve permitting flow through the tubular body portion only from the inlet portion to the outlet portion;

b) a relief valve portion joined to the tubular body portion, the relief valve portion having a central chamber, the central chamber having a single common ambient air conduit open to ambient air pressure;

c) a flow channel extending between the central chamber and the tubular body portion, the flow channel providing fluid communication between the tubular body portion and the central chamber;

d) a first relief valve mounted in the common ambient air conduit and configured to open if the pressure within the overpressure safety valve assembly diminishes below a predetermined level; and, e) a second relief valve mounted in the common ambient air conduit and configured to open if the pressure within the overpressure safety valve assembly exceeds a predetermined level;

f) in which the first and second relief valves are disposed in a side by side configuration and in which the first and second relief valves are each umbrella-type valves.

6. An overpressure safety valve comprising:

a) an elongated tubular body having an inlet, an outlet, and a regulator valve located within the tubular body to permit fluid flow only from the inlet to the outlet;

b) a relief valve section, joined to the tubular body, comprising a central chamber and a single common ambient air conduit;

c) a fluid flow channel between the central chamber and the tubular body at an outlet side of the regulator valve;

d) first and second relief valves, each mounted between the common ambient air conduit and the central chamber, the first relief valve mounted to open if pressure within the tubular body diminishes below a first predetermined level, and the second relief valve mounted to open if the pressure within the tubular body exceeds a second predetermined level.

7. The overpressure safety valve of claim 1 in which the regulator valve is a duckbill valve.

8. The overpressure safety valve of claim 1 in which the first and second relief valves are mounted side by side.

9. The overpressure safety valve of claim 1 in which at least one of the first and second relief valves is an umbrella valve.

* * * * *